United States Patent [19]
McCarthy et al.

[11] Patent Number: 5,349,952
[45] Date of Patent: Sep. 27, 1994

[54] PHOTOPLETHYSMOGRAPHICS USING PHASE-DIVISION MULTIPLEXING

[75] Inventors: Rex McCarthy, Newbury Park; Robert Smith, Corona, both of Calif.

[73] Assignee: Sensormedics Corp., Yorba Linda, Calif.

[21] Appl. No.: 665,594

[22] Filed: Mar. 5, 1991

[51] Int. Cl.$^5$ .............................................. A61B 5/00
[52] U.S. Cl. ..................... 128/633; 128/666; 356/41; 364/413.03
[58] Field of Search .................... 128/633, 664–665; 356/39–41; 250/339; 364/413.03

[56] References Cited

U.S. PATENT DOCUMENTS

| | | |
|---|---|---|
| 4,653,498 | 3/1987 | New, Jr. et al. ............ 128/633 |
| 4,807,630 | 2/1987 | Malinouskas ............... 128/633 |
| 4,907,876 | 3/1990 | Suzuki et al. ............... 128/633 |
| 4,942,877 | 7/1990 | Sakai et al. ................. 128/633 |

FOREIGN PATENT DOCUMENTS 8804155  6/1988  World Int. Prop. O. .......... 128/633

OTHER PUBLICATIONS

*Modern Digital and Analog Communication Systems*, B. P. Lahti–pp. 224–225, ©1989 Holt, Reinehart, and Winston Inc. Philadelphia.

*Primary Examiner*—Kyle L. Howell
*Assistant Examiner*—Robert L. Nasser, Jr.
*Attorney, Agent, or Firm*—Lyon & Lyon

[57] ABSTRACT

First and second carrier signals, distinguishable by phase, are respectively applied to infrared and red energy emitters. A detector receives the sum of the energy after modulation at the infrared and red wavelengths. The signal received by the detector is then demultiplexed into its original first and second components, thereby allowing determining of both the infrared and red modulation components. The first and second carrier signals may comprise time-varying periodic signals with identical frequency and frequency spectra, such as a pair of sine waves which are indistinguishable except by phase and amplitude. A 90° phase difference is preferred, but any phase other than 0 or an integer multiple of 180° is workable. A carrier frequency which avoids excessive interference from ambient light is preferred.

56 Claims, 2 Drawing Sheets

PHOTOPLETHYSMOGRAPHICS USING PHASE-DIVISION MULTIPLEXING

BACKGROUND OF THE INVENTION

1. Field of the Invention

This invention relates to photoplethysmographics. More specifically, this invention relates to phase-division multiplexing and demultiplexing of signals for infrared and red absorption of blood.

2. Description of Related Art

It is well known in the art to collect photoplethysmographic data simultaneously at a plurality of energy wavelengths. For example, blood oxygen concentration may be measured by determining absorption by a patient's tissues on infrared and red light; the degree of absorption is typically different for these two wavelengths. Infrared and red light are emitted into the patient's tissues (e.g., by infrared and red LEDs) and the total energy received to be detected by a single detector (e.g., a photodiode). However, one problem is that the signal produced by the detector must be processed to separate the infrared and red portions from each other.

One method of the prior art is shown in U.S. Pat. No. 4,407,290. Time-division multiplexing is used to alternately switch on the infrared and red emitters, at a frequency greater than the patient's pulse rate. The detector signal is then separated into infrared and red portions by sampling in synchrony with the on/off switching of the infrared and red emitters.

While this method successfully separates the infrared and red portions, it generally requires that sampling the detector signal must be synchronized with the on/off switching of the infrared and red emitters. It is also difficult while using this method to compensate for noise sources such as ambient light and electromagnetic interference.

A second method of the prior art is shown in U.S. Pat. No. 4,800,885. The infrared and red emitters are driven at two different frequencies. The detector signal is then separated into infrared and red portions by filtering at those two different frequencies.

While this method successfully separates the infrared and red portions, the method described in the patent requires demultiplexing signals which are phase-synchronized with the multiplexing frequencies, and produces a higher power output than the time-division multiplexing method. Also, while this method may avoid noise sources at predetermined and known frequencies, it is difficult to compensate for noise sources which were not known before the multiplexing frequencies were chosen, particularly because two separate frequencies which are free of interference must be chosen.

SUMMARY OF THE INVENTION

The invention provides a method of photoplethysmographics by phase-division multiplexing (as defined herein) and demultiplexing of signals for infrared and red absorption of blood. First and second carrier signals, distinguishable by phase, are respectively applied to infrared and red energy emitters. A detector receives the sum of the energy after modulation at the infrared and red wavelengths. The signal received by the detector is then demultiplexed into its original first and second components, thereby allowing determining of both the infrared and red modulation components.

In a preferred embodiment, the first and second carrier signals may comprise time-varying periodic signals with identical frequency and frequency spectra, such as a pair of sine waves which are indistinguishable except by phase and amplitude. A 90° phase difference is preferred, but any phase other than 0 or an integer multiple of 180° is workable. Also, a carrier frequency which avoids excessive interference from ambient light is preferred, such as 30 Hz.

DESCRIPTION OF THE PREFERRED EMBODIMENT

An embodiment of this invention may be used together with inventions which are disclosed in a copending application titled "PHOTOPLETHYSMOGRAPHICS USING ENERGY-REDUCING WAVEFORM SHAPING", U.S. patent application Ser. No. 07/664,782, filed the same day in the name of the same inventors, hereby incorporated by reference as if fully set forth herein.

Figure 1:
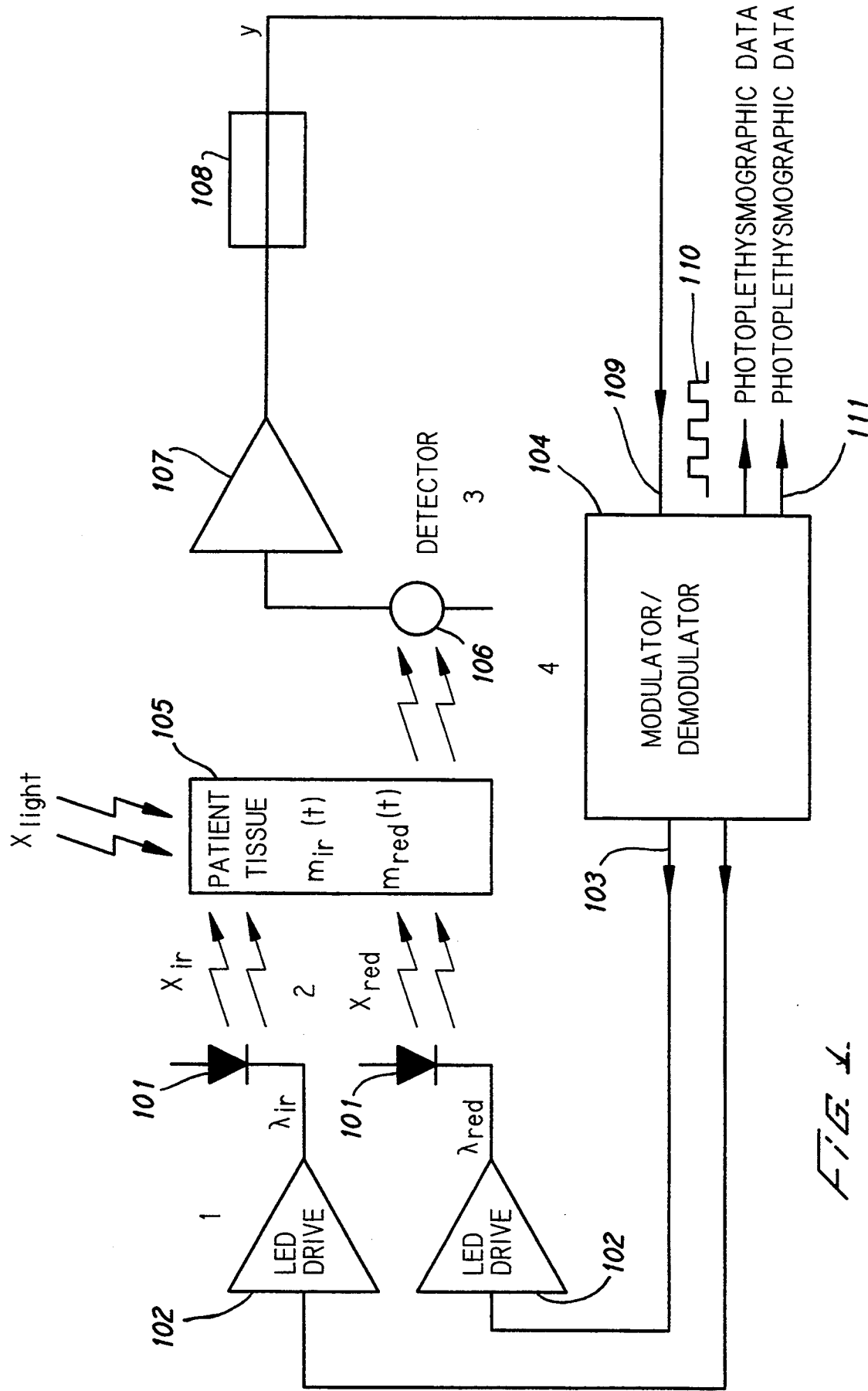
FIG. 1 shows a block diagram of a photoplethysmographic system comprising an embodiment of the invention.

FIG. 1 shows a block diagram of a photoplethysmographic system comprising an embodiment of the invention.

A plurality of energy emitters 101 may each be tuned to a separate wavelength. In a preferred embodiment for measuring blood oxygen, one of the emitters 101 may comprise an infrared light emitter and may operate at a wavelength of about 880 nanometers; another one of the emitters 101 may comprise a red light emitter and may operate at a wavelength of about 656 nanometers. (As used herein, "light" refers to electromagnetic energy of any wavelength, whether visible or not.) However, it may occur that other wavelengths may be useful, such as for measuring blood carbon dioxide, blood carbon monoxide, other blood gas concentrations, blood glucose, or more generally, other chemical and-/or physical concentrations.

Figure 2:
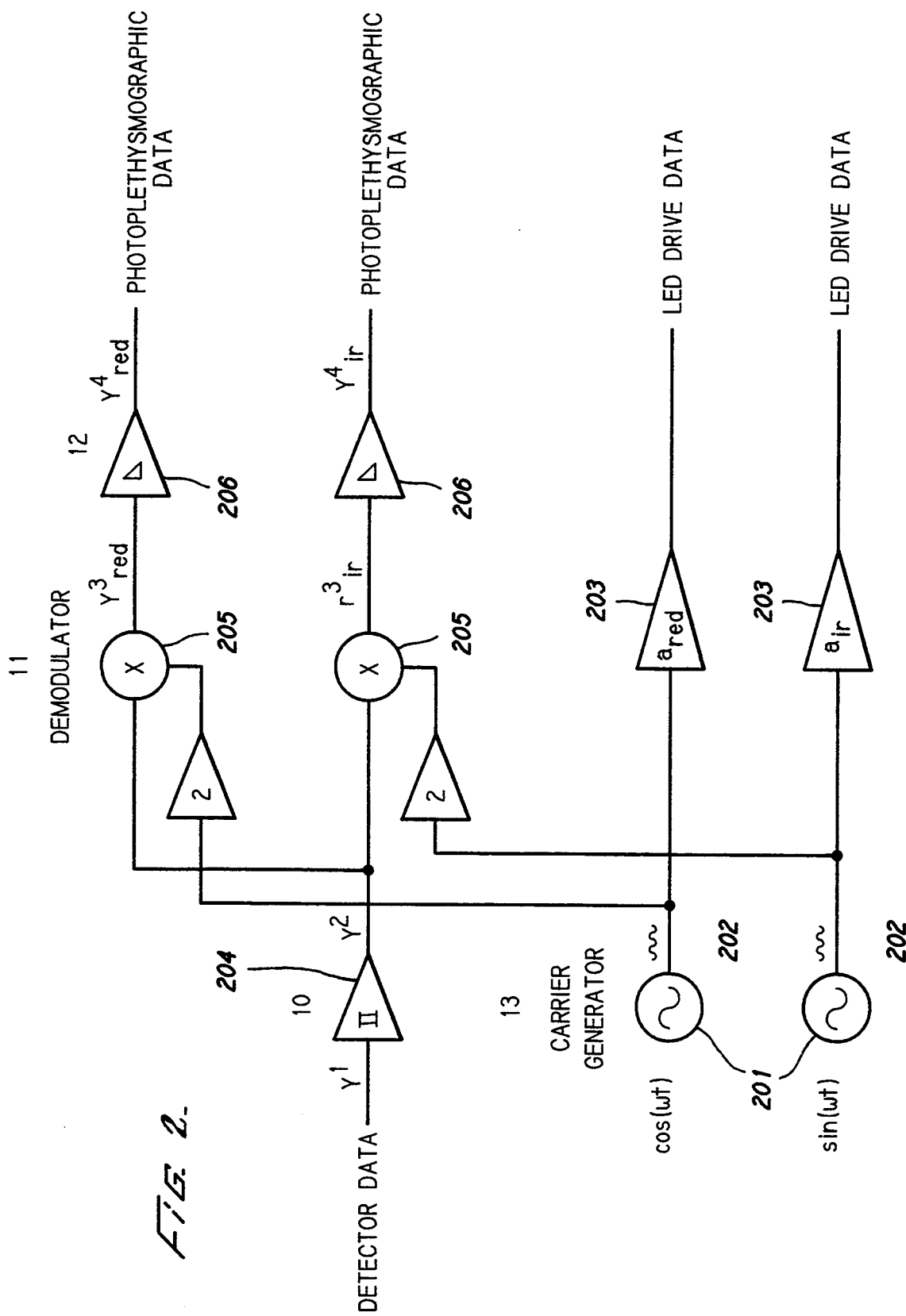
FIG. 2 shows a block diagram of the phase-division multiplexer and demultiplexer of an embodiment of the invention.

In a preferred embodiment, each of the emitters 101 may comprise an LED (such as part number OPC-8803 made by Marktech International Corp. for the infrared LED and part number MT1500-PUR made by Marktech International Corp. for the red LED), as is well known in the art, and may be coupled by means of an LED driver 102, as is well known in the art, to a carrier output 103 of a mux/demux circuit 104 (see FIG. 2).

Energy from the emitters 101 is applied to a tissue section 105 of a patient. In a preferred embodiment for measuring blood oxygen, the tissue section 105 is preferably chosen such that energy from the emitters 101 passes through the patient's blood vessels, such as an end of the patient's finger, the patient's earlobe, or (for neonates) the patient's hand or foot. The tissue section 105 may modulate the energy from the emitters 101, as is well known in the art, e.g., by absorbing some of the energy at each wavelength. Typically, energy may be modulated by transmission through the tissue section 105, but it may occur that energy may be modulated by reflection or by other means.

A detector 106 receives energy after modulation by the tissue section 105 and generates an output signal which indicates the total energy received. In a preferred embodiment, the detector 106 may comprise a photodiode (such as part number OSI-1140 made by Opto Sensors, Inc.) as is well known in the art. An output of the detector 106 is amplified by an amplifier 107 and coupled by means of a filter 108 to a detector input 109 of the mux/demux circuit 104.

The mux/demux circuit 104 generates a data output signal 110 at a data output 111, for each energy wavelength, which indicates the modulation which the tissue section 105 applied to that energy wavelength. In a preferred embodiment for measuring blood oxygen, information such as blood oxygen concentration may be calculated from the output signal, as is well known in the art.

Phase-division Multiplexing

Phase-division multiplexing, as used herein, is defined as follows. In phase-division multiplexing, a plurality of carrier signals are constructed, each of which may comprise a mixture of carrier components, and which are distinguishable by phase. (In a preferred embodiment, the carrier signals are identical except for phase.) Each carrier signal may be separately modulated, and the resultants summed. Thereafter, the separate modulations may be recovered from the sum, as disclosed herein.

In a preferred embodiment, a first carrier $\alpha$ may comprise a sine wave, e.g., $\cos(2\pi f1\ t)$, and a second carrier $\beta$ may comprise a sine wave which is phase-shifted with respect to the first carrier, e.g., $\sin(2\pi f1\ t)$. Alternatively, the first carrier e may comprise a sum of two or more carrier components, e.g., $\cos(2\pi f1\ t)+\cos(2\pi f2\ t)$, and the second carrier $\beta$ may comprise a sum of two or more carrier components which is distinguishable from the first carrier by phase, e.g., $\cos(2\pi f1\ t+\phi 1)+\cos(2\pi f2\ t+\phi 2)$. Possibly, f2 may comprise a harmonic of f1, but this is not required.

The following relations describe separate modulation of each carrier signal, with a 90° phase difference:

$$\alpha = \cos(w\ t) \qquad (112)$$

$$\beta = \sin(w\ t) \qquad (113)$$

$$\sigma = m1\alpha + m2\beta \qquad (114)$$

where w is a carrier frequency; m1 is a first modulating effect (e.g., at an infrared wavelength); m2 is a second modulating effect (e.g., at a red wavelength); and $\sigma$ is a detected sum of the modulated carrier signals $\alpha$, $\beta$ The detected sum $\sigma$ is separately multiplied by twice the first carrier $\alpha$ and by twice the second carrier $\beta$:

$$2\alpha\sigma = m1 + m1\cos(2w\ t) + m2\sin(2w\ t) \qquad (115)$$

$$2\beta\sigma = m2 - m2\cos(2w\ t) + m1\sin(2w\ t) \qquad (116)$$

These products $2\alpha\sigma$ and $2\beta\sigma$ are filtered to recover m1 and m2.

The following relations describe separate modulation of each carrier signal, with a phase difference other than 90°:

$$\alpha = \cos(w\ t) \qquad (117)$$

$$\beta = \cos(w\ t + \phi) \qquad (118)$$

$$\sigma = m1\alpha + m2\beta \qquad (119)$$

where w is the carrier frequency; m1 is the first modulating effect (e.g., at an infrared wavelength); m2 is the second modulating effect (e.g., at a red wavelength); and $\sigma$ is the detected sum of the modulated carrier signals $\alpha$, $\beta$ The detected sum $\sigma$ is separately multiplied by twice the first carrier $\alpha$ and by twice the second carrier $\beta$:

$$2\alpha\sigma = m1 + m1\cos(2w\ t) + m2\cos(\phi) + m2\cos(2w\ t+\phi) \qquad (120)$$

$$2\beta\sigma = m2 + m2\cos(2w\ t+2\phi) + m1\cos(\phi) + m1\cos(2w\ t+\phi) \qquad (121)$$

These products $2\sigma\alpha$ and $2\sigma\beta$ are filtered to recover m1* and m2*.

$$m1^* = m1 + m2\cos(\phi) \qquad (122)$$

$$m2^* = m1\cos(\phi) + m2 \qquad (123)$$

or $$\begin{bmatrix} 1 & \cos(\phi) \\ \cos(\phi) & 1 \end{bmatrix} \begin{bmatrix} m1 \\ m2 \end{bmatrix} = \begin{bmatrix} m1^* \\ m2^* \end{bmatrix} \qquad (124)$$

or $$KM = M^* \qquad (125)$$

where K is a phase-dependent matrix as shown; M is a vector of modulation effects m1, m2; and M* is a vector of modulated carrier component parts m1*, m2*

Separate components m1, m2 may be demultiplexed by multiplying by the left multiplicative inverse of the phase-dependent matrix K:

$$M = K^{-1}M^* \qquad (126)$$

or $$M = K^{-1}KM \qquad (127)$$

Multiplexer/Demultiplexer Circuit

FIG. 2 shows a block diagram of the phase-division multiplexer and demultiplexer of an embodiment of the invention.

The disclosure herein shows a case where both the first carrier and the second carrier each comprise pure sine waves which differ in phase by exactly 90°. However, applying this disclosure to cases where either the first or the second carrier is not a pure sine wave, or where a component of the first and second carriers differs in phase by other than exactly 90° would be clear to one of ordinary skill in the art, after perusal of the specification, drawings and claims herein.

A carrier generator 201 generates a plurality of carrier signals 202. In a preferred embodiment, each carrier signal 202 is allocated to one emitter wavelength. Thus, there is a first carrier signal 202 allocated to infrared and a second carrier signal 202 allocated to red. Also, in a preferred embodiment, each carrier signal 202 may comprise a sine wave with frequency f1, as disclosed herein, and the two carrier signals 202 may differ in phase by exactly 90°.

In a preferred embodiment, f1 is chosen such that interference from noise sources, such as ambient light and electromagnetic interference, is minimized. In a preferred embodiment, f1 is also chosen such that a bandwidth of about 4 Hz for the modulating effects of the tissue section 105 is allowed. Frequencies in the range of about 30–40 Hz, such as 31.5 Hz, are preferred, but it would be clear to one of ordinary skill in the art, after perusal of the specification, drawings and claims herein, that other frequencies would be workable, and are within the scope and spirit of the invention.

It would also be clear to one of ordinary skill in the art, after perusal of the specification, drawings and claims herein, that there is no requirement that the components of the carrier signal 202 must be sine waves. Other types of carrier components, such as square waves or other waveforms, would be workable, and are within the scope and spirit of the invention.

It would be clear to one of ordinary skill in the art, after perusal of the specification, drawings and claims herein, that there is no requirement that the first carrier and the second carrier must differ in phase by exactly 90°. Other phase differences other than 0 or an integer multiple of 180° would be workable, and are within the scope and spirit of the invention.

It would also be clear to one of ordinary skill in the art, after perusal of the specification, drawings and claims herein, that the invention may be adapted to measurement of other constituents, such as blood carbon dioxide, blood carbon monoxide, other blood gas concentrations, blood glucose, or more generally, other chemical and/or physical concentrations.

Each carrier signal 202 is coupled by means of a brightness amplifier 203, for adjusting the brightness of a corresponding emitter 101, to the corresponding carrier output 103 of the mux/demux circuit 104.

The detector input 109 is coupled, by means of a first filter 204, for removing components at frequencies other than the carrier frequency, to a plurality of demultiplexer elements 205 for demultiplexing the modulated first carrier signal 202 from the modulated second carrier signal 202. A second input of each of the demultiplexer elements 205 is coupled to one of the carrier signals 202. The carrier signals 202 are multiplied, and the products are coupled, by means of a second filter 206, for removing components other than baseband, which shows the modulating effects of the tissue section 105, to produce the data output signals 110.

The data output signals 110 each indicate the modulation effect for the corresponding carrier signal 202, as multiplied by a correction by the corresponding brightness amplifier 203. Each data output signal 110 is coupled to the corresponding data output 111 of the mux/demux circuit 104.

In a preferred embodiment, signal generation and signal manipulation as described herein are preferably performed by a digital microprocessor (such as part number DSP56001 made by Motorola) operating under software control. It would be clear to one of ordinary skill in the art, after perusal of the specification, drawings and claims herein, that programming a standard digital microprocessor to perform signal generation and signal manipulation as described herein would be a straightforward task and would not require undue experimentation.

It would be clear to one of ordinary skill in the art, after perusal of the specification, drawings and claims herein, that the invention may be combined with known methods of computing blood oxygen concentration and other blood gas values from the data output signals 110 which are produced. Providing a system which combines the invention with such known methods would be a straightforward task, after perusal of the specification, drawings and claims herein, and would not require undue experimentation.

In a preferred embodiment, the first filter 204 and the second filter 206 should each exhibit a known phase response. Otherwise phase errors might introduce crosstalk between the infrared and red data output signals 110.

Alternative Embodiments

While preferred embodiments are disclosed herein, many variations are possible which remain within the concept and scope of the invention, and these variations would become clear to one of ordinary skill in the art after perusal of the specification, drawings and claims herein.

We claim:

1. An instrument for evaluating the concentration of a constituent in an object by measuring the transmission of light of two wavelengths therethrough, comprising:
   (a) first and second light emitter means for emitting light at respective, first and second different wavelengths;
   (b) modulator/driver means for driving the light emitter means simultaneously with respect first and second carriers which vary as a function of time, the carriers being continuous time-varying signals of the same carrier frequency and having a phase difference other than 0° degrees and other than an integer multiple of 180° degrees, wherein said first and second light emitter means have at least one time period when they are both substantially emitting;
   (c) detector means disposed to receive light from the first and second light emitter means after it has passed through the object, for generating a resulting detector signal carrying information relating to transmission of the object at both wavelengths;
   (d) demodulator means for generating, in response to the detector signal, in a first channel, a first demodulated signal which is a sum of a component proportional to the object's transmission at the first wavelength and one or more carrier modulated components, and, in a second channel, a second demodulated signal which is a sum of a component proportional to the object's transmission at the second wavelength and one or more carrier modulated components; and
   (e) a demodulated signal filter, coupled to said first and second channels, wherein said demodulated signal filter filters out carrier modulated components of the signals from the first and second channels.

2. An instrument as defined in claim 1, additionally comprising detector filter means for filtering frequencies other than around the carrier frequency from the detector signal prior to it being processed by the demodulator.

3. An instrument for evaluating the concentration of a constituent in object by measuring the transmission of light of two wavelengths therethrough, comprising:
   (a) first and second light emitter means for emitting light at respective, first and second different wavelengths;

(b) modulator/driver means for driving the light emitter means simultaneously with respective first and second sinusoidal carriers which are of the same carrier frequency and having a phase difference other than 0° degrees and other than an integer multiple of 180° degrees, wherein said first and second light emitter means have at least one time period when they are both substantially emitting;

(c) detector means disposed to receive light from the first and second light emitter means after it has passed through the object, for generating a resulting detector signal carrying information relating to transmission of the object at both wavelengths;

(d) demodulator means for, in a first channel, multiplying the detector signal with a sinusoidal signal in phase with the first carrier to generate a first demodulated signal which is a sum of a component proportional to the object's transmission at the first wavelength and one or more carrier modulated components, and for, in a second channel, multiplying the detector signal with a sinusoidal signal in phase with the second carrier to generate a second demodulated signal which is a sum of a component proportional to the object's transmission at the second wavelength and one or more carrier modulated components; and (e) a demodulated signal filter, coupled to said first and second channels, wherein said demodulated signal filter filters out carrier modulated components of the signals from the first and second channels.

4. An instrument as defined in claim 3 wherein said modulator/driver means comprises means for driving said light emitter means with first and second carriers with a carrier frequency which is greater than the bandwidth of the object's transmission signal.

5. An instrument as defined in claim 3, additionally comprising detector filter means for filtering frequencies other than around the carrier frequency from the detector signal prior to it being processed by the demodulator.

6. An instrument as defined in claim 3 or 2 or 4 or 5 wherein the demodulated signal filter is a low pass filter which filters signals above the bandwidth of the object's transmission signal.

7. An instrument as defined in claim 3 or 2 or 4 or 5 which additionally comprises an interpreter, coupled to said demodulator signal filter, which evaluates the concentration of oxygen from the demodulated signal filter output.

8. Apparatus as in claim 3, wherein said detector means comprises means for detecting light which has been applied to a body structure.

9. A method for evaluating the concentration of a constituent in an object, comprising:

(a) simultaneously driving a first and a second light emitter, which emit light at different wavelengths, with respective first and second carriers which vary continuously as a function of time and are of the same carrier frequency and having a phase difference other than 0° degrees and other than an integer multiple of 180° degrees, wherein said first and second light emitters have at least one time period when they are both substantially emitting;

(b) directing the light from the emitters through the object;

(c) receiving the light from the emitters at a detector after it has passed through the object, which detector generates a detector signal carrying information relating to transmission of the object at both wavelengths;

(d) demodulating the detector signal to generate, in a first channel, a first demodulated signal which is a sum of a component proportional to the object's transmission at the first wavelength and one or more carrier modulated components, and, in a second channel, a second demodulated signal which is a sum of a component proportional to the object's transmission at the second wavelength and one or more carrier modulated components;

(e) filtering out carrier modulated components of the first and second demodulated signals and (f) evaluating the concentration of oxygen from the demodulated and filtered signals.

10. A method for evaluating the oxygen concentration in a body structure of an animal, comprising:

(a) simultaneously driving a first and a second light emitter, which emit light in the red and infra-red regions, respectively, with respective first and second sinusoidal carriers of the same carrier frequency and having a phase difference other than 0° degrees and other than an integer multiple of 180° degrees, wherein said first and second light emitters have at least one time period when they are both substantially emitting;

(b) directing the light from the emitters through the body structure;

(c) receiving the light from the emitters at a detector after it has passed through the body structure, which detector generates a detector signal carrying information relating to transmission of the body structure at both wavelengths;

(d) demodulating the detector signal to generate, in a first channel, a first demodulated signal which is a sum of a component proportional to the body structure's transmission of red light, and one or more carrier modulated components, and, in a second channel, a second demodulated signal which is a sum of a component proportional to the body structure's transmission of infra-red light and one or more carrier modulated components;

(e) filtering out carrier modulated components of the first and second demodulated signals;

(f) evaluating the concentration of oxygen from the demodulated and filtered signals.

11. A method as defined in claim 9 or 10 wherein the first and second light emitters are driven with carriers of a frequency greater than the bandwidth of the object's transmission signal.

12. A device for collecting photoplethysmographic data, comprising means for generating a first and a second signal, said first and second signals being distinguishable by phase;

means for simultaneously applying said first and second signals to a modulating medium, said means for simultaneously applying comprising a first and second emitter, said first and second emitters having at least one time period when they are both substantially emitting;

means for detecting a composite signal at an output of said modulating medium, said modulating medium having a first and a second modulating effect; and means for generating a first and a second output signal responsive to said composite signal, said first output signal indicating said first modulating effect and said second output signal indicating said second modulating effect, said means for generating comprising means for multiplying at least part of said composite signal with a continuous time-varying signal.

13. A device as in claim 12, wherein said means for generating comprises means for generating first and second signals which are periodic time-varying signals with identical periods.

14. A device as in claim 12, wherein said means for generating comprises means for generating first and second signals which have identical frequency components.

15. A device as in claim 12, wherein said means for detecting comprises a photodiode.

16. A device as in claim 12, wherein said means for detecting a composite signal comprises means for detecting a composite signal comprising a sum of said first modulating effect applied to said first signal and said second modulating effect applied to said second signal.

17. A device as in claim 12, comprising means for determining, in response to a set of photoplethysmographic data, blood gas data.

18. A device as in claim 12, comprising means for determining, in response to a set of photoplethysmographic data, at least one of blood oxygen, blood carbon dioxide, or blood carbon monoxide.

19. A device as in claim 12, wherein said means for generating comprises means for generating at least one comprising a plurality of component signals.

20. A device as in claim 19, wherein said means for generating comprises means for generating at least one signal comprising a plurality of component signals, at least one of said component signals comprising a sum of at least one of a sine wave or, a square wave.

21. A device as in claim 12, wherein said means for applying comprises a plurality of light-emitters.

22. A device as in claim 12, wherein said means for applying comprises a plurality of light-emitters tuned to a plurality of wavelengths.

23. A device as in claim 12, wherein said means for applying comprises means for directing at least one of said first and second signals at animal tissue.

24. A device as in claim 12, wherein said means for applying comprises means for directing at least one of said first and second signals toward at least one of blood, blood vessels, bone marrow, ligament, muscle, or skin.

25. A device as in claim 12, wherein said means for detecting a composite signal comprises means for detecting a composite signal comprising a result of a plurality of modulating effects, wherein at least one of said modulating effects comprises amplitude modulation.

26. A device as in claim 12, wherein said means for detecting a composite signal comprises means for detecting a composite signal comprising a result of a plurality of modulating effects, wherein said modulating effects comprise an amplitude modulation effect which varies with energy wavelength.

27. A device as in claim 12, wherein said means for detecting a composite signal comprises means for detecting a composite signal comprising a result of a plurality of modulating effects, wherein at least one of said modulating effects comprises a time-varying component.

28. A device as in claim 12, wherein said means for detecting a composite signal comprises means for detecting a composite signal comprising a result of a plurality of modulating effects, wherein at least one of said modulating effects comprises a time-varying component which is correlated with a biological process.

29. A device as in claim 12, wherein said means for detecting a composite signal comprises means for detecting a composite signal comprising a result of a plurality of modulating effects, wherein at least one of said modulating effects comprises at least one transmission response of a modulating medium.

30. Apparatus as in claim 12, wherein said means for generating comprises
means for generating said first signal comprising a first sine wave; and
means for generating said second signal comprising a second sine wave, said second sine wave being delayed 90° degrees from said first sine wave.

31. Apparatus as in claim 12, wherein said means for detecting comprises
means for sampling said composite signal at a rate higher than a frequency component of said first signal.

32. Apparatus as in claim 12, wherein said means for generating a first and second output signal comprises
means for multiplying at least a part of said composite signal by a continuous time-varying signal corresponding to at least one of said carrier signals; and
means for filtering.

33. Apparatus as in claim 12, wherein said means for generating a first and second output signal comprises
first means for multiplying said composite signal by said first carrier signal;
first means for filtering a resultant of said first means for multiplying;
second means for multiplying said composite signal by said second carrier signal; and
second means for filtering a resultant of said first means for multiplying.

34. A device for collecting photoplethysmographic data, comprising
means for phase-division multiplexing a plurality of modulating signals;
means for modulating a resultant of said means for phase-division multiplexing; and
means for phase-division demultiplexing said plurality of signals, in response to a resultant of said means for modulating, said means for phase-division demultiplexing comprising means for multiplying at least part of a resultant of said means for modulating with a continuous time-varying signal.

35. A device as in claim 34, wherein said means for phase-division multiplexing comprises means for phase-division multiplexing a plurality of modulating signals which comprise an infrared wavelength modulating signal and a red wavelength modulating signal.

36. A device as in claim 34, wherein said means for phase-division multiplexing and said means for phase-division demultiplexing collectively include means for generating a plurality of carrier signals.

37. A method of collecting photoplethysmographic data, comprising the steps of
generating a first and a second signal, said first and second signals being distinguishable by phase;
simultaneously applying said first and second signals to a modulating medium, including substantially emitting in response to said first signal and substantially emitting in response to said second signal, both during at least one time period;

detecting a composite signal at an output of said modulating medium, said modulating medium having a first and a second modulating effect; and generating a first and a second output signal responsive to said composite signal, said first output signal indicating said first modulating effect and said second output signal indicating said second modulating effect, said step of generating comprising multiplying at least part of said composite signal with a continuous time-varying signal.

38. A method as in claim 37, wherein said first and second signals are periodic time-varying signals with identical periods.

39. A method as in claim 37, wherein said first and second signals have identical frequency components.

40. A method as in claim 37, wherein said modulating medium comprises animal tissue.

41. A method as in claim 37, wherein said modulating medium comprises at least one of blood, blood vessels, bone marrow, ligament, muscle, or skin.

42. A method as in claim 37, wherein said composite signal comprises a sum of said first modulating effect applied to said first signal and said second modulating effect applied to said second signal.

43. A method as in claim 37, comprising generating a set of photoplethysmographic data comprising blood gas data.

44. A method as in claim 37, comprising generating a set of photoplethysmographic data comprises at least one of: blood oxygen, blood carbon dioxide or, blood carbon monoxide.

45. A method as in claim 37, wherein at least one of said first and second signals comprises a plurality of component signals.

46. A method as in claim 45, wherein at least one of said component signals comprises a sum of at least one of a sine wave or, a square wave.

47. A method as in claim 37, wherein at least one of said modulating effects comprises amplitude modulation.

48. A method as in claim 37, wherein said modulating effects comprise an amplitude modulation effect which varies with energy wavelength.

49. A method as in claim 37, wherein at least one of said modulating effects comprises a time-varying component.

50. A method as in claim 37, wherein at least one of said modulating effects comprises a time-varying component which is correlated with a biological process.

51. A method as in claim 37, wherein at least one of said modulating effects comprises at least one transmission response of a modulating medium.

52. A method of collecting photoplethysmographic data, comprising the steps of phase-division multiplexing a plurality of modulating signals;

modulating a resultant of said step of phase-division multiplexing; and phase-division demultiplexing said plurality of signals, in response to a resultant of said step of modulating, said step of phase-division demultiplexing comprising multiplying at least part of a resultant of said step of modulating with a continuous time-varying signal.

53. A method as in claim 52, wherein said plurality of modulating signals comprises an infrared wavelength modulating signal and a red wavelength modulating signal.

54. A device for collecting photoplethysmographic data, comprising means for generating a first and a second signal, said first and second signals being distinguishable by phase;

means for applying said first and second signals to a modulating medium, said means for applying comprising a first and second emitter, said first and second emitters having at least one time period when they are both substantially emitting;

means for detecting a composite signal at an output of said modulating medium, said modulating medium having a first and a second modulating effect;

means for sampling said composite signal at a rate higher than a frequency component of said first signal; and means for generating a first and a second output signal responsive to said composite signal, said first output signal indicating said first modulating effect and said second output signal indicating said second modulating effect.

55. Apparatus as in claim 54, wherein said means for generating a first and second output signal comprises means for multiplying at least a part of said composite signal by a continuous time-varying signal corresponding to at least one of said carrier signals; and means for filtering.

56. Apparatus as in claim 54, wherein said means for generating a first and second output signal comprises first means for multiplying said composite signal by said first carrier signal;

first means for filtering a resultant of said first means for multiplying;

second means for multiplying said composite signal by said second carrier signal; and second means for filtering a resultant of said first means for multiplying.

* * * * *